United States Patent
Katz et al.

(10) Patent No.: US 11,759,783 B2
(45) Date of Patent: Sep. 19, 2023

(54) ASSAY DEVICE

(71) Applicant: NOVAMED LTD., Jerusalem (IL)

(72) Inventors: Emil Katz, Savyon (IL); Gadi Porath, Kiryat Tivon (IL); Ural Rashitov, Jerusalem (IL)

(73) Assignee: Novamed Ltd., Jerusalem (IL)

( * ) Notice: Subject to any disclaimer, the term of this patent is extended or adjusted under 35 U.S.C. 154(b) by 300 days.

(21) Appl. No.: 15/777,922

(22) PCT Filed: Nov. 24, 2016

(86) PCT No.: PCT/IL2016/051266
§ 371 (c)(1),
(2) Date: May 22, 2018

(87) PCT Pub. No.: WO2017/090043
PCT Pub. Date: Jun. 1, 2017

(65) Prior Publication Data
US 2018/0339292 A1    Nov. 29, 2018

(30) Foreign Application Priority Data
Nov. 26, 2015 (IL) .......................................... 242807

(51) Int. Cl.
*B01L 3/00* (2006.01)
*G01N 33/543* (2006.01)

(52) U.S. Cl.
CPC ............ *B01L 3/5029* (2013.01); *B01L 3/502* (2013.01); *G01N 33/54366* (2013.01);
(Continued)

(58) Field of Classification Search
CPC .................. B01L 3/5029; B01L 3/502; B01L 2200/0689; B01L 2300/044;
(Continued)

(56) References Cited

U.S. PATENT DOCUMENTS

| 4,769,333 A | 9/1988 | Dole |
| 4,862,899 A | 9/1989 | Bucaro |

(Continued)

FOREIGN PATENT DOCUMENTS

| AU | 2013277910 B2 | 11/2017 |
| CN | 104582571 A | 4/2015 |

(Continued)

OTHER PUBLICATIONS

Corrected version of the International Search Report for PCT/IL2016/051266, 8 pages, dated Feb. 2, 2017.

(Continued)

*Primary Examiner* — Matthew D Krcha
*Assistant Examiner* — Jacqueline Brazin
(74) *Attorney, Agent, or Firm* — Roach Brown McCarthy & Gruber, P.C.; Kevin D. McCarthy (57) ABSTRACT

The present invention relates to an assay device for determining the presence and/or amount of an analyte of interest in a sample, the assay device comprising: a) a housing that includes a liquid receiving unit that is adapted to accommodate one or more types of liquid; b) a mixing chamber adapted for containing a solution that is a product of one more types of liquid, and for receiving a sample to interact with said solution; c) an actuating lid which is capable of being actuated to enable the transfer of the liquid into the mixing chamber; and d) an assay means that is in fluid communication with said mixing chamber for determining the presence and/or amount of an analyte of interest in the sample after the interaction of said sample with said solution in the mixing chamber.

15 Claims, 6 Drawing Sheets

(52) U.S. Cl.
CPC . *B01L 2200/026* (2013.01); *B01L 2200/0689* (2013.01); *B01L 2300/044* (2013.01); *B01L 2300/049* (2013.01); *B01L 2300/0663* (2013.01); *B01L 2300/0867* (2013.01); *B01L 2300/12* (2013.01)

(58) Field of Classification Search
CPC ....... B01L 2300/049; B01L 2300/0663; B01L 2300/0867; B01L 2300/12; G01N 33/54366
USPC ......................................................... 422/411
See application file for complete search history.

(56) References Cited

U.S. PATENT DOCUMENTS

| | | | |
|---|---|---|---|
| 5,128,104 A | | 7/1992 | Murphy et al. |
| 5,415,994 A | | 5/1995 | Imrich |
| 6,464,939 B1 | * | 10/2002 | Bachand ............ A61B 10/0051 422/411 |
| 7,241,417 B2 | | 7/2007 | Lee |
| 7,544,324 B2 | | 6/2009 | Tung |
| 7,837,939 B2 | | 11/2010 | Tung |
| 7,932,099 B2 | * | 4/2011 | Egan ..................... G01N 33/558 435/7.1 |
| 9,562,921 B2 | | 2/2017 | Moran |
| 2002/0085958 A1 | | 7/2002 | Nemcek et al. |
| 2007/0087357 A1 | * | 4/2007 | Clark ............... G01N 33/54386 435/6.11 |
| 2008/0171052 A1 | | 7/2008 | Bianchi et al. |
| 2008/0199851 A1 | * | 8/2008 | Egan ..................... B01L 3/5029 435/5 |
| 2008/0260581 A1 | | 10/2008 | Rosman et al. |
| 2010/0255609 A1 | * | 10/2010 | Rutter ................... B01L 3/5023 436/518 |
| 2014/0286837 A1 | | 9/2014 | Bartfeld |
| 2015/0148261 A1 | | 5/2015 | Frei et al. |
| 2015/0182156 A1 | * | 7/2015 | Engbersen ........... G01N 33/491 435/7.94 |
| 2016/0169779 A1 | * | 6/2016 | Taira ....................... B01L 3/508 422/549 |

FOREIGN PATENT DOCUMENTS

| | | | |
|---|---|---|---|
| EP | 1621886 A1 | | 2/2006 |
| EP | 1628567 B1 | | 8/2010 |
| JP | H 07-506665 A | | 7/1995 |
| JP | 2003-500651 A | | 1/2003 |
| JP | 2004-523579 A | | 8/2004 |
| JP | 2007-518994 A | | 7/2007 |
| RU | 2485497 C2 | | 6/2013 |
| WO | WO-0062929 A2 | * 10/2000 | ....... G01N 27/44743 |
| WO | 2008/075044 A2 | | 6/2008 |
| WO | 2009044088 A1 | | 4/2009 |
| WO | 2010/056185 A1 | | 5/2010 |
| WO | 2012/025729 A1 | | 3/2012 |

OTHER PUBLICATIONS

International Preliminary Report on Patentability for PCT/IL2016/051266, 13 pages, dated Feb. 28, 2018.
International Search Report for PCT/IL2016/051266, 8 pages, dated Feb. 28, 2018.
Written Opinion of the International Searching Authority for PCT/IL2016/051266, 5 pages, dated Feb. 2, 2017.
Office action from the Japanese patent office in a counterpart foreign application—Japanese application No. 2018-526802—dated Oct. 27, 2020, 4 pages; and a 3 page English machine translated version.

* cited by examiner

ASSAY DEVICE

FIELD OF THE INVENTION

The present invention relates to the field of diagnostic immunoassays. More particularly, the invention relates to a device for carrying out a lateral flow assay on a sample.

BACKGROUND OF THE INVENTION

An assay is an investigative (analytic) procedure (e.g., in laboratory medicine, pharmacology, etc.) for qualitatively assessing or quantitatively measuring the presence or amount or the functional activity of a target entity (the analyte). The analyte can be a drug or biochemical substance or a cell in an organism or organic sample. The measured entity is generally called the analyte, or the measure and or the target of the assay. The assay usually aims to measure an intensive property of the analyte and express it in the relevant measurement unit (e.g. molarity, density, functional activity in enzyme international units, degree of some effect in comparison to a standard, etc.).

Assays have become a routine part of modern medical, environmental, pharmaceutical, forensic and many other businesses at various scales from industrial to curbside or field level. Simple disposable assay devices for the detection of an analyte in a liquid sample are well known. For example, U.S. Pat. No. 5,415,994 discloses devices, methods, and kits for treatment and detection of analytes requiring pretreatment in samples. The methods of detecting such analytes comprise inserting a swab containing the sample in an extraction chamber of the device; inserting an extraction solution to the extraction chamber; observing accumulation of label in the capture zone of the device; and determining therefrom the presence or absence of the analyte in the sample. However, a major drawback of such device is that in order to use the device, it is required to manually insert the extraction solution. U.S. Pat. No. 7,241,417 discloses a device comprising a sample containing unit comprising a sample container, said sample container being closed off at one end by a bottom wall, said bottom wall having a hole sealed by a plug; and a housing located under said sample container and capable of holding a test strip, said sample containing unit and said housing being coupled so as to allow rotation one relative to the other, said housing comprising a cutting arrangement capable of cutting said plug; wherein rotation of said sample containing unit and said housing one relative to the other results in said cutting arrangement cutting said plug, thereby unplugging the hole in said bottom wall. However, such device lacks the ability to prevent the insertion of the sample stick prior to the preparation of the mixed solution, which may result in negative or positive errors. Furthermore, such device lacks the ability to cause for a delay that required in many cases for the mixture and interaction of the sample (i.e., analyte) with reactants (i.e., reagents).

It is an object of the present invention to provide an assay device which is capable of preparing the solution prior to the insertion of the sampling device.

It is another object of the present invention to provide an assay device which is capable of delaying the mixture and/or interaction of the sample with reactants.

Other objects and advantages of the invention will become apparent as the description proceeds.

SUMMARY OF THE INVENTION

The present invention relates to an assay device for determining the presence and/or amount of an analyte of interest in a sample, the assay device comprising:

a) a housing that includes a liquid receiving unit that is adapted to accommodate one or more types of liquid in a way that each type of liquid is being stored in a separate liquid chamber, wherein each liquid chamber having a first opening that is sealed with an openable liquid seal;

b) a mixing chamber located at said housing which is adapted for containing a solution that is a product of the one more types of liquid as received from each liquid chamber, wherein said mixing chamber is further adapted to receive a sample to interact with said solution;

c) a lid which is capable of being actuated to enable the puncturing or removal of the openable liquid seal (of each liquid chamber) by a corresponding puncturing element that is located within said housing; and d) an assay means that is in fluid communication with said mixing chamber for determining the presence and/or amount of an analyte of interest in the sample after the interaction of said sample with said solution in the mixing chamber.

According to an embodiment of the invention, the actuation of the lid is obtained by a pushable mechanism that enables to press/push said lid toward the housing, and thereby to cause the openable seal of each chamber to be punctured or removed by the opening elements that are located within the interior of said housing. The opening elements are in the interior of said housing with respect to the location of the sealed opening of each chamber.

According to an embodiment of the invention, the lid comprises an opening through which a sample can be inserted into the mixing chamber, in order to be able to interact with the solution.

According to an embodiment of the invention, the opening for the insertion of the sample is blocked, in order to prevent the insertion of the sample prior to the actuation of the lid and the delivery of the liquids into the mixing chamber. According to an embodiment of the invention, the actuation of the lid unblocks said opening.

According to an embodiment of the invention, the lid is configured in such a way that the insertion of the sample into the mixing chamber is enabled only after the extraction of the liquid from each chamber into said mixing chamber.

According to an embodiment of the invention, the device further comprises a delay mechanism for delaying the interaction of the sample with the solution within the mixing chamber.

According to an embodiment of the invention, the housing includes a plurality of liquid chambers, each adapted to contain a liquid or at least one of them contains a liquid sensitive reagent and the remaining chambers contain a liquid.

According to an embodiment of the invention, the solution in the mixing chamber is a mixed solution obtained by the liquids received from the plurality of chambers.

According to an embodiment of the invention, at least one of the liquid chambers having a second opening for enabling to fill said liquid chamber with a liquid, wherein said second opening is being sealed by the lid.

According to an embodiment of the invention, the second opening is located at the top end of the liquid chamber.

According to an embodiment of the invention, the first opening is located at the bottom or the lower end of the liquid chamber.

According to an embodiment of the invention, at least one liquid chamber is an integral part of the housing or the liquid receiving unit.

According to an embodiment of the invention, at least one liquid chamber is a standalone container that is adapted to be inserted into the liquid receiving unit.

According to an embodiment of the invention, the openable liquid seal is a layer that is made of a material having low fluid permeability such as metal, alloy or polymer layer. According to an embodiment of the invention, the openable liquid seal includes a bondable backing layer such as a lacquer or a laminate to enable said seal to be bonded to the liquid chamber.

DETAILED DESCRIPTION OF THE INVENTION

Reference will now be made to several embodiments of the present invention, examples of which are illustrated in the accompanying figures. Wherever practicable similar or like reference numbers may be used in the figures and may indicate similar or like functionality. The figures depict embodiments of the present invention for purposes of illustration only. One skilled in the art will readily recognize from the following description that alternative embodiments of the structures and methods illustrated herein may be employed without departing from the principles of the invention described herein.

The term "sample" refers herein to any specimen, preferably a fluid, potentially containing an analyte.

The term "sample mixing liquid" refers to a liquid or solution that interacts with the sample. Interaction of the liquid with the sample may result in a dilution, a reaction, a binding event or a suspension.

Referring now to FIGS. 1-8, in a first aspect, the invention provides an assay device 1 for determining the presence and/or amount of an analyte of interest in a sample. The assay device 1 comprises an actuating lid 2, a liquid receiving unit 20 that may include one or more liquid chambers such as a first chamber 11 and a second chamber 12, a mixing chamber 14, an assay means 5 for determining the presence and/or amount of an analyte of interest in the sample, and a housing 4 that serves to house one or more components of the device, such as the assay means 5 and the liquid receiving unit 20. In some embodiments, part of the housing may form the liquid receiving unit 20.

The first chamber 11 may contain a first liquid and the second chamber 12 may contain a second liquid, wherein each of the first and second chambers 11, 12 is sealed with an openable liquid seal 21 and 22 (see FIGS. 8A-8C), respectively. For example, in this embodiment, the openable liquid seals 21 and 22 are located at the bottom end of each chamber 11, 12, respectively.

Figure 1:
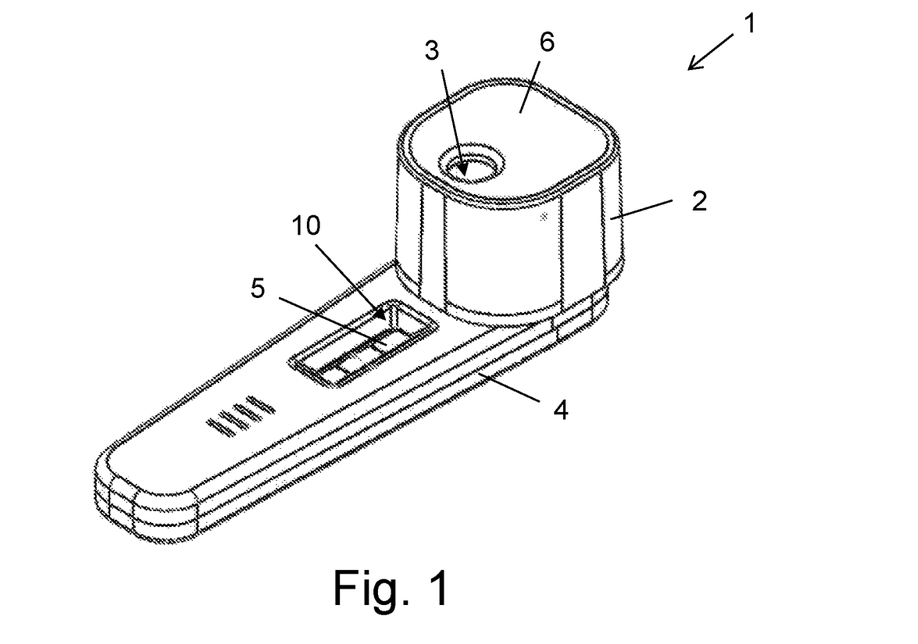
FIG. 1 schematically illustrates a perspective view of an assay device with an actuating lid, according to an embodiment of the invention.
Figure 2:
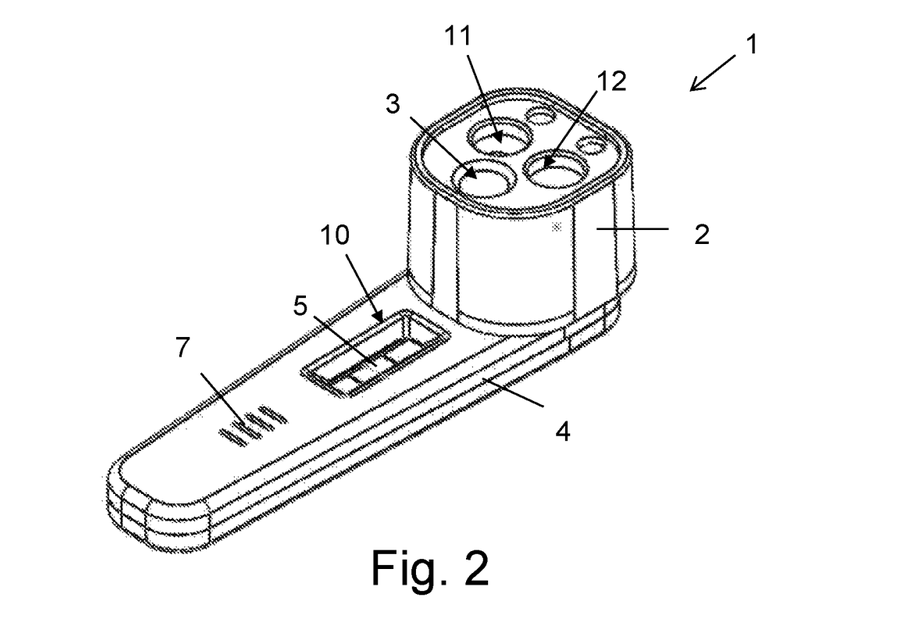
FIG. 2 schematically illustrates a perspective view of the assay device without the top cover of the pushable actuator head.
Figure 3:
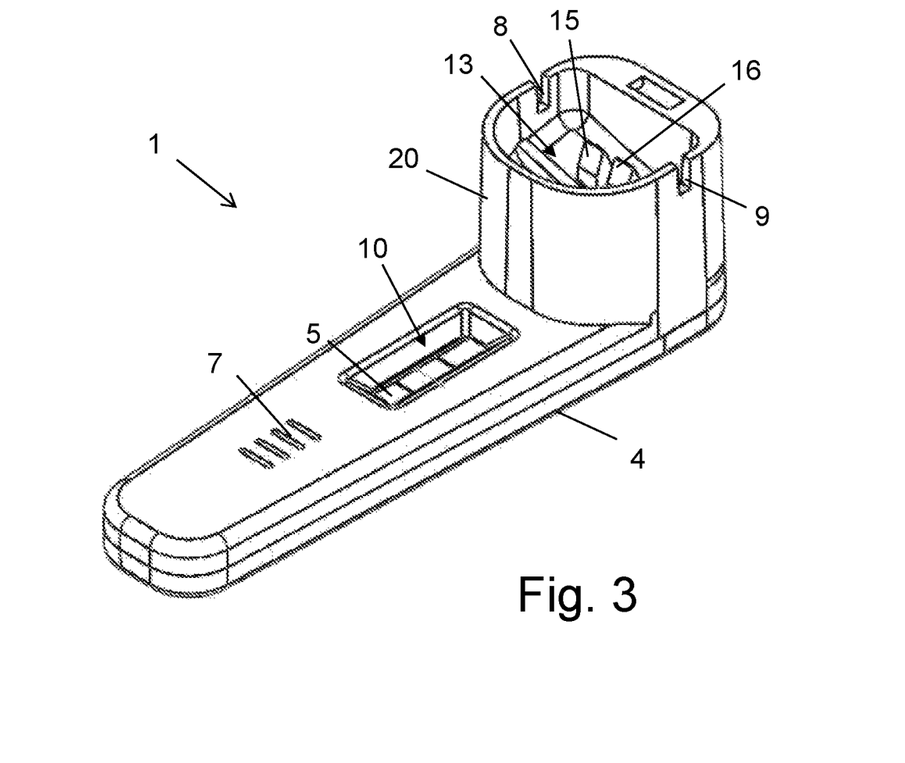
FIG. 3 schematically illustrates a perspective view of the assay device without the actuating lid.
Figure 4:
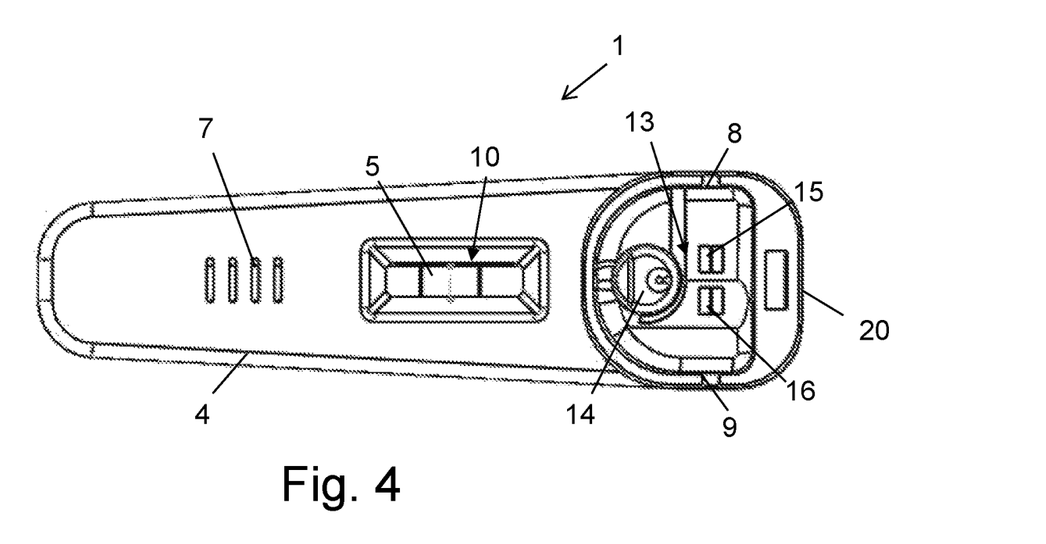
FIG. 4 schematically illustrates a top view of the assay device of FIG. 3.
Figure 5:
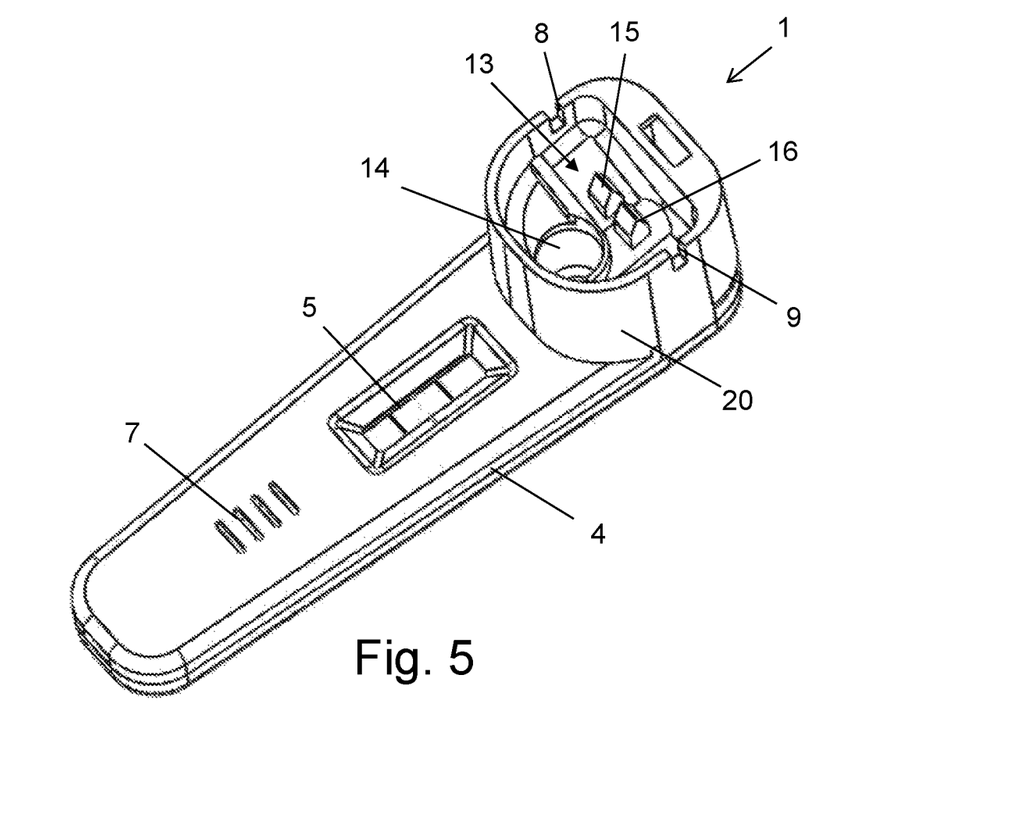
FIG. 5 schematically illustrates another perspective view of the assay device without the actuating lid.
Figure 6A:
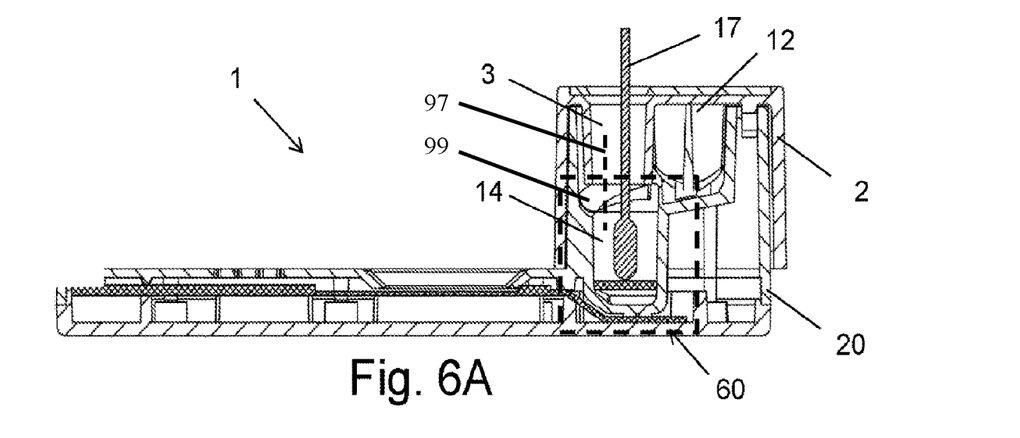
FIG. 6A schematically illustrates a cross-sectional view of the assay device with a sampling swab inserted into a mixing chamber, according to an embodiment of the present invention.
Figure 6B:
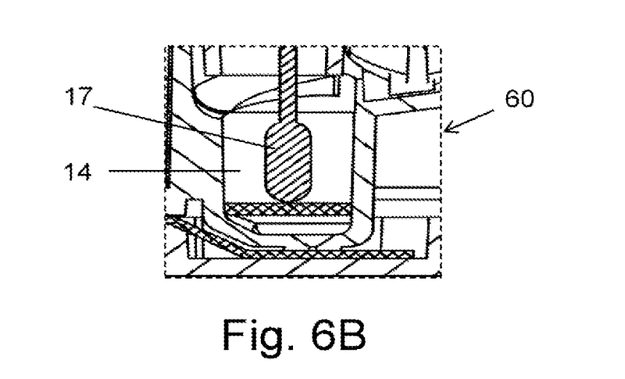
FIG. 6B schematically illustrates a magnify view of the sampling swab within the mixing chamber.
Figure 7:
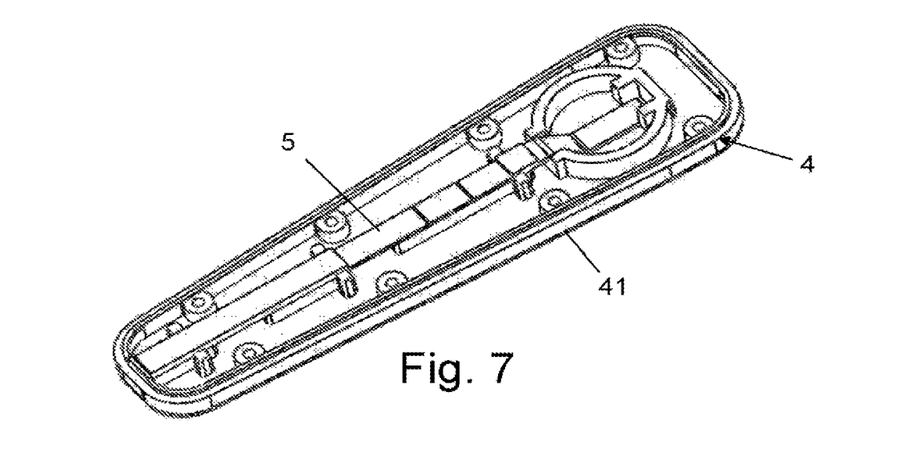
FIG. 7 schematically illustrates the base unit of the assay device of FIG. 1, according to an embodiment of the invention.
Figure 8A:
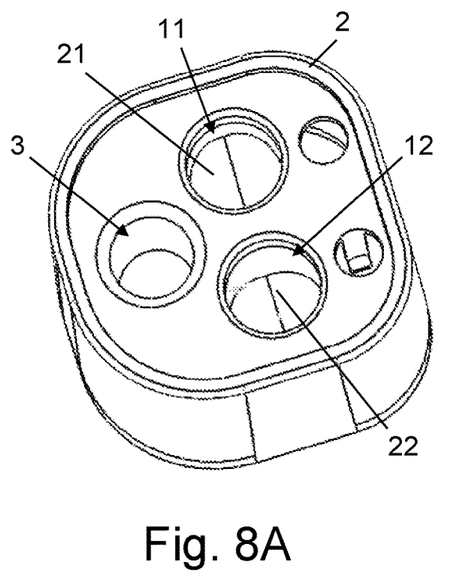
FIG. 8A schematically illustrates a perspective view of the actuating lid, according to an embodiment of the invention.
Figure 8B:
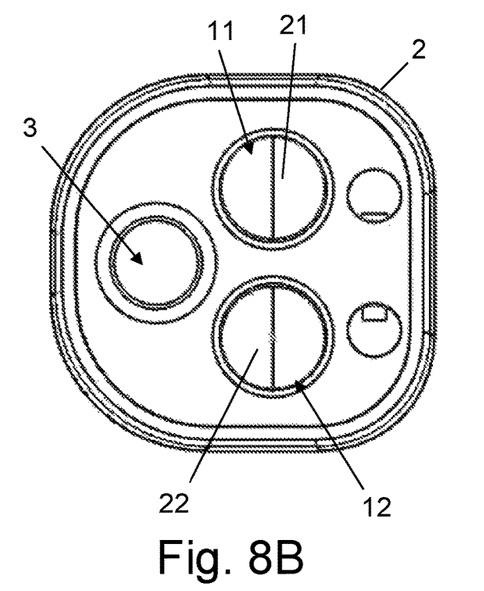
FIG. 8B schematically illustrates a top view of the actuating lid.
Figure 8C:
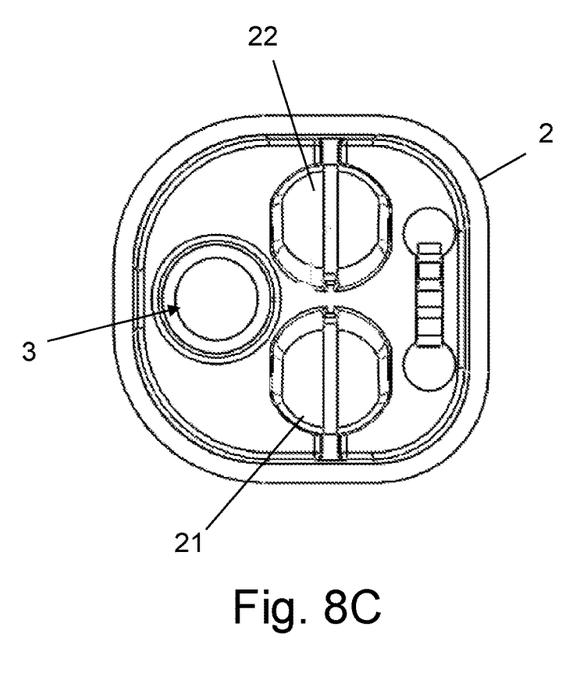
FIG. 8C schematically illustrates a bottom view of the actuating lid.

The sample receiving liquid mixing chamber 14 is used for containing a mixed solution of the first and second liquids as received from the chambers 11, 12. The mixing chamber 14 is also adapted to receive the sample into the liquid mixing chamber 14 (e.g., by using a sample swab 17 as shown in FIGS. 6A and 6B and emphasized by the section indicated by numeral 60). In this embodiment, the assay device 1 is configured in such a way that the insertion of the sample into the mixing chamber 14 will be allowed only after the preparation of the mixed solution by the liquids received from the first and second chambers 11, 12.

Figure 10A:
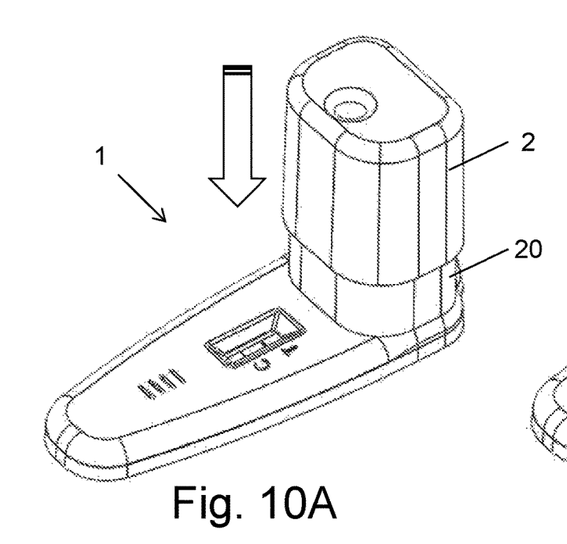
FIG. 10A schematically illustrates the assay device prior to the actuation of the actuating lid.
Figure 10B:
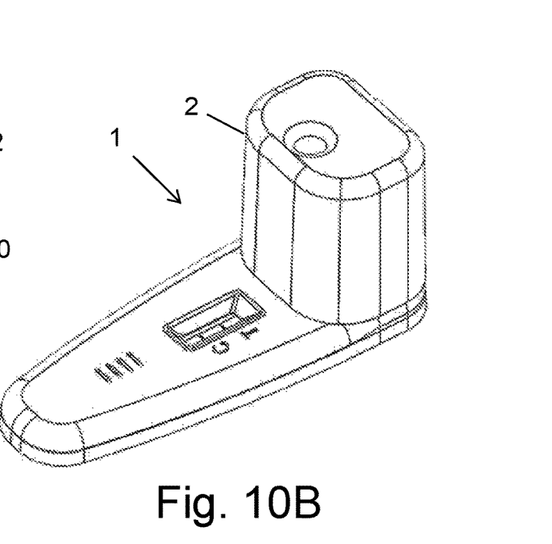
FIG. 10B schematically the assay device after the actuation of the actuating lid.

Each of the openable seals 21, 22 refers to a seal which is capable of being removed or punctured in order to enable the liquid within the first and second chambers 11, 12 to flow into the mixing chamber 14. The openable seal 21, 22 may be puncturable. In this embodiment, the lid 2 is capable of being actuated to cause the openable seals 21, 22 to be punctured or removed. For example, lid 2 can be actuated by applying pressure on its top portion (as shown with respect to FIGS. 10A and 10B) in order to transmit force that may cause the openable seals 21, 22 to be punctured or removed.

The openable seals 21, 22 can be punctured or removed by an opening means 15, 16 capable of opening the liquid seals 21, 22, respectively. The opening means 15, 16 refer to a means which is capable of opening the openable seals 21, 22 either directly or indirectly. The opening means 15, 16 may be a mechanism which serves to puncture the seal. In some embodiments, the opening means 15, 16 is a puncturing means and the openable seal is puncturable.

In some embodiments, the opening means 15, 16 are puncturing elements that may be shaped so as to easily puncture a puncturable material, thereby minimizing the force required by the user to puncture the material. For example, the top end of each puncturing element 15, 16 may form a sharp point which is the first point of contact between the puncturing element and the puncturable material (i.e., the openable seals 21, 22). Each puncturing element 15, 16 may comprise a sharpened lower surface capable of cutting (thereby puncturing) the puncturable material.

The top end of each puncturing elements 15, 16 faces the opening of each chamber 11, 12 respectively to be inserted through the opening of the corresponding chamber. The sharp end ensures that the puncturable material is punctured. Each puncturing element may include an upper projection defining the surface of contact between the puncturing element and the chamber to be inserted. Preferably, the upper projection presents a minimal surface area of contact with the punctured surface.

According to some embodiment of the invention, the liquid at least at one of the chambers 11, 12 may be sprayed out of the chamber (e.g., towards the mixing chamber 14 by using a spraying arrangement (e.g., dedicated nozzle at the bottom of chamber 11).

Each of the first and second chambers 11, 12 contains a liquid which is sealed within the container by the first and second liquid seals 21, 22, respectively. The liquid may be aqueous in nature. Although the present invention is described herein with reference to liquids, it will be appreciated that the present invention is equally applicable for fluids.

In this embodiment, the actuating lid 2 comprises the first and second chambers 11, 12 and an opening access 3 for enabling the swab 17 to be inserted into the mixing chamber 14. The first seal 21 seals an opening of the first chamber 11 and may be provided in proximity to the opening means 15 and the second seal 22 seals an opening of the second chamber 12 and may be provided in proximity to the opening means 15. The chambers 11, 12 fluidically separate the liquids from the mixing chamber 14 and the assay means 5 as long as they are remain sealed. The actuation of the lid 2 may result in mixing of the liquid contained in the respective liquid chambers 11, 12 (e.g., mixing of a liquid in one liquid chamber 11 with a liquid sensitive reagent in another liquid chamber 12). In order to ensure the mixture of the liquids from both chambers 11, 12 an inner surface 13 at the interior of hosing 4 has an inclined and spiral-like (a.k.a., a helical inner surface 99 having a helical axis 97) form that forces the liquids to flow in spiral or twisted manner towards the mixing chamber 14. Such a spiral flow manner may facilitate the mixing of both liquids, preferably, prior to the insertion of the sampling device (e.g., swab 17) into the mixing chamber 14.

In this embodiment, the actuation of lid 2 is obtained by a pushable mechanism that enables to press/push the lid 2 toward the housing 4 of device 1, and thereby to cause the openable seals 21, 22 to be punctured or removed by the opening means 15, 16, which are located within the interior of housing 4, with respect to the location of the sealed opening of chambers 11, 12. For example, lid 2 may be displaced along a fixed track as formed by notches 8 and 9 (see FIGS. 3-5). In other words, lid 2 may have two possible positions an initial position (i.e., pre-press) and a pressing position which cause the puncturing of the openable seals 21, 22. A puncture force is need in order to actuate lid 2 and to puncture the openable seals 21, 22. In some embodiments, at the initial position the opening 13 may be blocked in order to prevent the insertion of the sampling device prior to the mixture of the liquids. Opening 13 may be unblocked manually (e.g., by removable of a sealing layer on top of it), or may be unblocked automatically during the actuation of lid 2 (e.g., by automatically breaking or removing a sealing layer).

The assay device 1 may comprise a plurality of liquid chambers such as 11, 12 each containing a liquid or wherein one of them contains a liquid sensitive reagent and the remaining chambers contain a liquid. Where a plurality of liquid chambers are provided, the liquids may be maintained in each chamber and separated from each other by the openable liquid seal of each chamber, such that insertion of a sampling device (e.g., swab 17) into the mixing chamber 14, after the actuation of the lid 2, results in the interaction of the sampling device with the liquids in each chamber only after the mixture of the liquids in the mixing chamber 14.

Actuation of lid 2 allows a user to simply and easily insert an item (i.e., a sampling device such as swab 17) into the mixing chamber 14 via opening 13, without the item itself directly puncturing the puncturable seal. Thus the need to use excessive force in order to contact the item with the fluid provided within the mixing chamber 14 is minimized.

According to an embodiment of the invention, the device comprises a delay mechanism for delaying the interaction of the sample with the solution within the mixing chamber 14. The delay mechanism can be a sponge, a suitable orifice or any other mechanism or element capable of delaying the sample to access the mixing chamber. The delay mechanism can be provided as a buffer at an opening of the mixing chamber 14 that is in communication with opening 13 in the lid 2, through which the sample is inserted into the device 1.

The first and/or second seals 21, 22 may be chosen from a material having low fluid permeability such as a metal, alloy or polymer layer. The layer may have a thickness in the range of from about 15 to about 100 microns. The layer may further comprise a bondable backing layer such as a lacquer or a laminate to enable the layer to be bonded to the liquid chambers.

The assay device 1 may comprise one or more reagents appropriate for the assay in question. Examples of reagents may be chosen from, but not limited to, a binding reagent capable of binding to an analyte of interest, an enzyme, a surfactant, a buffer, an extraction reagent, a salt, a precipitation reagent, a viscosity modifying reagent and a lysing reagent. The binding reagent may be labelled with a detectable label. The one or more reagents may be provided within the liquid chambers. The reagents may be provided in the dry state or in the wet state.

The assay means 5 may comprise a liquid pathway such as a capillary channel, a microfluidic pathway, or a porous flow through carrier such as a lateral flow porous carrier. The liquid pathway may lead to a detection chamber or zone as indicated by numeral 10. The porous flow through carrier may comprise one or a plurality of porous carrier materials which in use are fluidically connected. The plurality of porous carrier materials may be the same or different. The plurality of porous carriers may at least partially overlap one another in a linear or stacked arrangement. The assay means 5 may comprise a lateral flow carrier material. The assay means 5 may comprise a plurality of liquid pathways each defining a separate flow path for the detection of an analyte. The analyte may be the same or different. Where a plurality of liquid pathways are provided they may have a common sample receiving portion such that liquid from the mixing chamber 14 is able to flow to each flow channel.

As will be appreciated by a person skilled in the art, the assay means 5 can be implemented using a variety of detection methods. For example, the assay means 5 may comprise one or more reagents appropriate for the assay in question. The one or more reagents may be chosen from a binding agent capable of binding to the analyte of interest, a reagent that is able to react with the analyte of interest, such as an enzyme, a reagent that is able to interact or otherwise react with the products of any interaction between the analyte of interest and a further reagent. The assay means 5 may comprise a detection zone 10 which is capable of detecting a product of the interaction or reaction of the analyte of interest and one or more reagents. Other methods can also be used such as immobilising a labelled binding reagent for an analyte of interest, the use of an enzyme for the analyte of interest, the use of an electron mediator for the enzyme or a colour developing reagent and/or a precipitation reagent, etc.

The analyte of interest to be determined by the assay device may be of a biological, industrial or environmental nature. The analyte may be of a mammalian, especially of a human origin. The analyte of interest may be any of significance including toxins, organic compounds, proteins, peptides, microorganisms, bacteria, viruses, amino acids, nucleic acids, carbohydrates, hormones, steroids, vitamins and drugs. The analyte may be one which requires a liquid pre-treatment step before being exposed to an assay means. The liquid treatment step may comprise one or more of, but not limited to, a dilution, a liquid suspension, an extraction, a binding reaction, a biochemical reaction, a chemical reaction, a buffering, a treatment with a surfactant. The pre-treatment step may be carried out by introducing the analyte of interest into the liquid container and allowing it to interact with the liquid container therein. The liquid container may comprise one or more reagents which enable a pre-treatment step to be carried out. In particular, analytes of interest include *Streptococcus* A, *Candida* organisms and bacterial vaginosis organisms.

The sample can be derived from any source, such as a physiological liquid, including blood, serum, plasma, saliva, sputum, ocular lens liquid, sweat, urine, milk, ascites liquid, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions, amniotic liquid, and the like.

Figure 9:
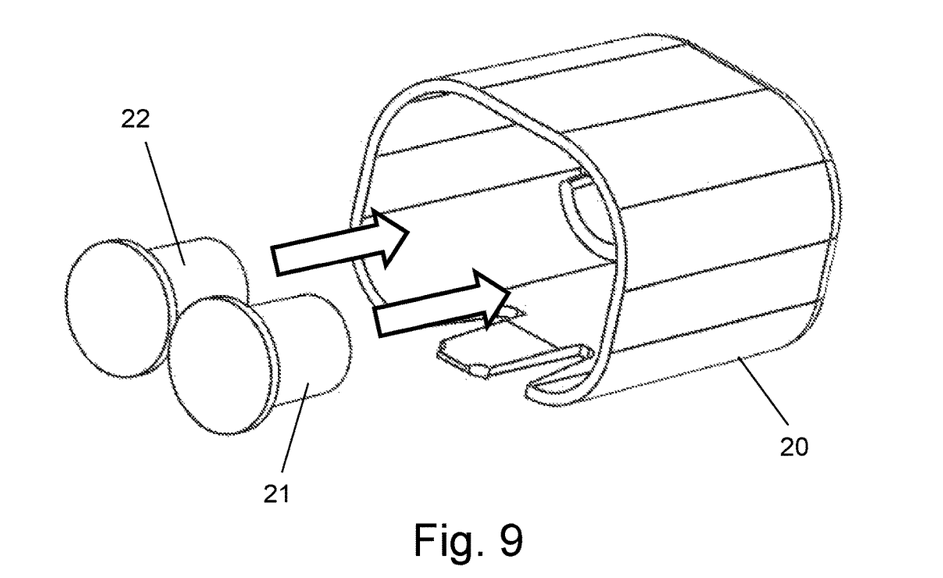
FIG. 9 schematically illustrates liquid chambers adapted to be inserted into a liquid receiving unit of the assay device, according to some embodiments of the present invention.

According to some embodiments, the one or more liquid chambers (such as chambers 11 and 12) can be standalone liquid storage containers that are adapted to be inserted into the liquid receiving unit 20, e.g., as shown in FIG. 9.

As will be appreciated by the skilled person the arrangement described in the figures results in an assay device which is capable of preparing the solution prior to the insertion of the sampling device.

All the above description and examples have been given for the purpose of illustration and are not intended to limit the invention in any way. Many different mechanisms and methods of analysis, can be employed, all without exceeding the scope of the invention.

The invention claimed is:

1. An assay device for determining the presence and/or amount of an analyte of interest in a sample, the assay device comprising:
  a) a housing comprising:
    a liquid receiving unit having at least a first liquid chamber and a second liquid chamber, and, optionally, an additional liquid chamber(s);
    wherein
      the first liquid chamber stores a liquid sensitive reagent, the second liquid chamber stores a liquid that is different from the liquid sensitive reagent, and each optional additional liquid chamber(s) stores a liquid that is different from any liquid stored in the first liquid chamber, the second liquid chamber, and any other optional additional liquid chamber(s), and
      the first liquid chamber, the second liquid chamber, and optional additional liquid chamber(s), each liquid chamber has a first opening, and each first opening (a) has an openable liquid seal and (b) is sealed with the openable liquid seal,
    said liquid receiving unit comprising:
      (i) a puncturing element;
      (ii) a liquid mixing chamber which is adapted for containing a solution that is a product of the liquids received from the first liquid chamber, the second liquid chamber, and optional additional liquid chamber(s), wherein said liquid mixing chamber is further adapted to receive a sample to interact with said solution; and
      (iii) a helical inner surface between said puncturing element and said liquid mixing chamber, said helical inner surface forcing the liquids from the first liquid chamber, the second liquid chamber, and optional additional liquid chamber(s) to flow downward towards the liquid mixing chamber while rotating around a helical axis of said helical inner surface, in order to facilitate the mixing of the liquids; and
    said housing further comprising:
      an assay test strip having a proximal end and a distal end wherein (a) positioned between the proximal end and the distal end is at least one detection zone containing at least one reagent, and (b) positioned between the proximal end and the at least one detection zone is a sample-solution loading area of the assay strip;
      the sample-solution loading area is in fluid communication with said liquid mixing chamber so when the sample-solution from the liquid mixing chamber is applied to the assay strip, the sample-solution flows along a liquid pathway from the sample-solution loading area toward the distal end and as the sample-solution passes the at least one detection zone, the at least reagent indicates the presence and/or amount of an analyte of interest in the sample; and
    the assay device further comprising:
      b) an actuating lid which is capable of being actuated to enable the puncturing or removal of each chamber's openable liquid seal by said puncturing element.

2. The device according to claim 1, in which the actuation of the actuating lid occurs by pressing and/or pushing said actuating lid toward the housing, and thereby to cause the openable seal of each liquid chamber to be punctured or removed by the opening elements that are located within the interior of said housing, with respect to the location of the sealed opening of each liquid chamber.

3. The device according to claim 1, in which the actuating lid comprises an opening through which a sample can be inserted into the liquid mixing chamber.

4. The device according to claim 3, in which the opening is blocked in order to prevent the insertion of the sample prior to the actuation of the actuating lid and the delivery of the liquids into the liquid mixing chamber.

5. The device according to claim 1, in which the actuating lid is configured in such a way that the insertion of the sample into the liquid mixing chamber is enabled only after the extraction of the liquid from each liquid chamber into said liquid mixing chamber.

6. The device according to claim 1, further comprising a second delay mechanism for delaying the interaction of the sample with the solution within the liquid mixing chamber.

7. The device according to claim 1, in which the first liquid chamber, the second liquid chamber, and optional additional liquid chamber(s) each has a second opening for enabling to fill said liquid chamber.

8. The device according to claim 7, in which the second opening is located at the top end of each liquid chamber.

9. The device according to claim 1, in which the first opening is located at the bottom or the lower end of each liquid chamber.

10. The device according to claim 1, in which the first liquid chamber and the second liquid chamber are an integral part of the housing or the liquid receiving unit.

11. The device according to claim 1, in which at least the first liquid chamber or the second liquid chamber is a standalone container that is adapted to be inserted into the liquid receiving unit.

12. The device according to claim 1, in which each openable liquid seal is a layer that is made of a material having low fluid permeability.

13. The device according to claim 12, in which the layer is made of metal, alloy or polymer layer.

14. The device according to claim 1, in which each openable liquid seal includes a bondable backing layer of a lacquer or a laminate to enable each chamber's openable liquid seal to be bonded to the respective liquid chamber.

15. The device according to claim 1, in which the form of the helical inner surface at the interior of said housing has an inclined and spiral-like form.

\* \* \* \* \*